(12) United States Patent
Phillips

(10) Patent No.: US 8,668,902 B2
(45) Date of Patent: Mar. 11, 2014

(54) COMPOSITION WITH ACTIVATED CARBON IN ORAL TREATMENT

(75) Inventor: David M. Phillips, St. Paul, MN (US)

(73) Assignee: Vapor Shield, Inc., Ham Lake, MN (US)

( * ) Notice: Subject to any disclaimer, the term of this patent is extended or adjusted under 35 U.S.C. 154(b) by 1421 days.

(21) Appl. No.: 11/756,019

(22) Filed: May 31, 2007

(65) Prior Publication Data

US 2007/0286821 A1 Dec. 13, 2007

Related U.S. Application Data

(60) Provisional application No. 60/812,175, filed on Jun. 8, 2006.

(51) Int. Cl.
*A61K 9/20* (2006.01)

(52) U.S. Cl.
USPC ............................................. 424/48; 424/464

(58) Field of Classification Search
USPC ........................................................ 424/464
See application file for complete search history.

(56) References Cited

U.S. PATENT DOCUMENTS

| | | | |
|---|---|---|---|
| 937,683 A | 10/1909 | Matweff | |
| 1,542,006 A | 6/1925 | Sauer | |
| 2,252,934 A | 8/1941 | Lautmann | |
| 3,332,783 A * | 7/1967 | Frey | 426/548 |
| 3,427,379 A | 2/1969 | Barry et al. | |
| 3,509,258 A | 4/1970 | Kuhnis et al. | |
| 3,642,986 A | 2/1972 | Welch et al. | |
| 3,917,821 A | 11/1975 | Manes | |
| 4,122,169 A | 10/1978 | Geils | |
| 4,761,284 A | 8/1988 | Nishimura | |
| 4,971,798 A | 11/1990 | Coia et al. | |
| 5,534,165 A | 7/1996 | Pilosof et al. | |
| 5,539,930 A | 7/1996 | Sesselmann | |
| 5,616,340 A * | 4/1997 | Ells et al. | 424/440 |
| 5,681,564 A | 10/1997 | Saulson | |
| 5,861,144 A | 1/1999 | Peterson et al. | |
| 5,874,067 A | 2/1999 | Lucas et al. | |
| 6,004,334 A | 12/1999 | Mythen | |
| 6,074,631 A * | 6/2000 | Tsuchiya et al. | 424/65 |
| 6,350,438 B1 | 2/2002 | Witt et al. | |
| 6,440,415 B1 * | 8/2002 | Johnson | 424/125 |
| 6,607,711 B2 | 8/2003 | Pedersen | |
| 6,696,047 B2 | 2/2004 | Scott et al. | |
| 6,861,049 B2 | 3/2005 | Harwood | |
| 2002/0132000 A1 * | 9/2002 | Saniez et al. | 424/467 |
| 2003/0012744 A1 | 1/2003 | Pedersen | |
| 2003/0129144 A1 | 7/2003 | Scott et al. | |
| 2003/0165441 A1 | 9/2003 | Alexander et al. | |
| 2003/0206876 A1 | 11/2003 | Buch | |
| 2004/0197278 A1 * | 10/2004 | Gonzales et al. | 424/48 |
| 2005/0084551 A1 | 4/2005 | Jensen et al. | |
| 2005/0191384 A1 * | 9/2005 | Bretl et al. | 426/3 |

OTHER PUBLICATIONS

Kirk-Othmer Concise Encyclopedia of Chemical Technology, 4$^{th}$ Edition, pp. 323-324, 1999.
Norit Activated Carbon webpage, www.norit-americas.com/1.11.5.htm, printed Jun. 8, 2006.
Stonybrook Outfitters LLC 2006 Catalog, Fatal Attractor Series.

* cited by examiner

*Primary Examiner* — Jeffrey S. Lundgren
*Assistant Examiner* — Chris Simmons
(74) *Attorney, Agent, or Firm* — Pauly, DeVries Smith & Deffner, L.L.C.

(57) ABSTRACT

In a personal care daily practice, common human malodor in breath can be treated and eliminated or substantially reduced through the use of a treatment comestible, lozenge, chewing gum or scraper prepared by combining a hardenable natural or artificial sweetener or gum base with an amount of activated carbon effective in reducing such malodors.

9 Claims, 1 Drawing Sheet

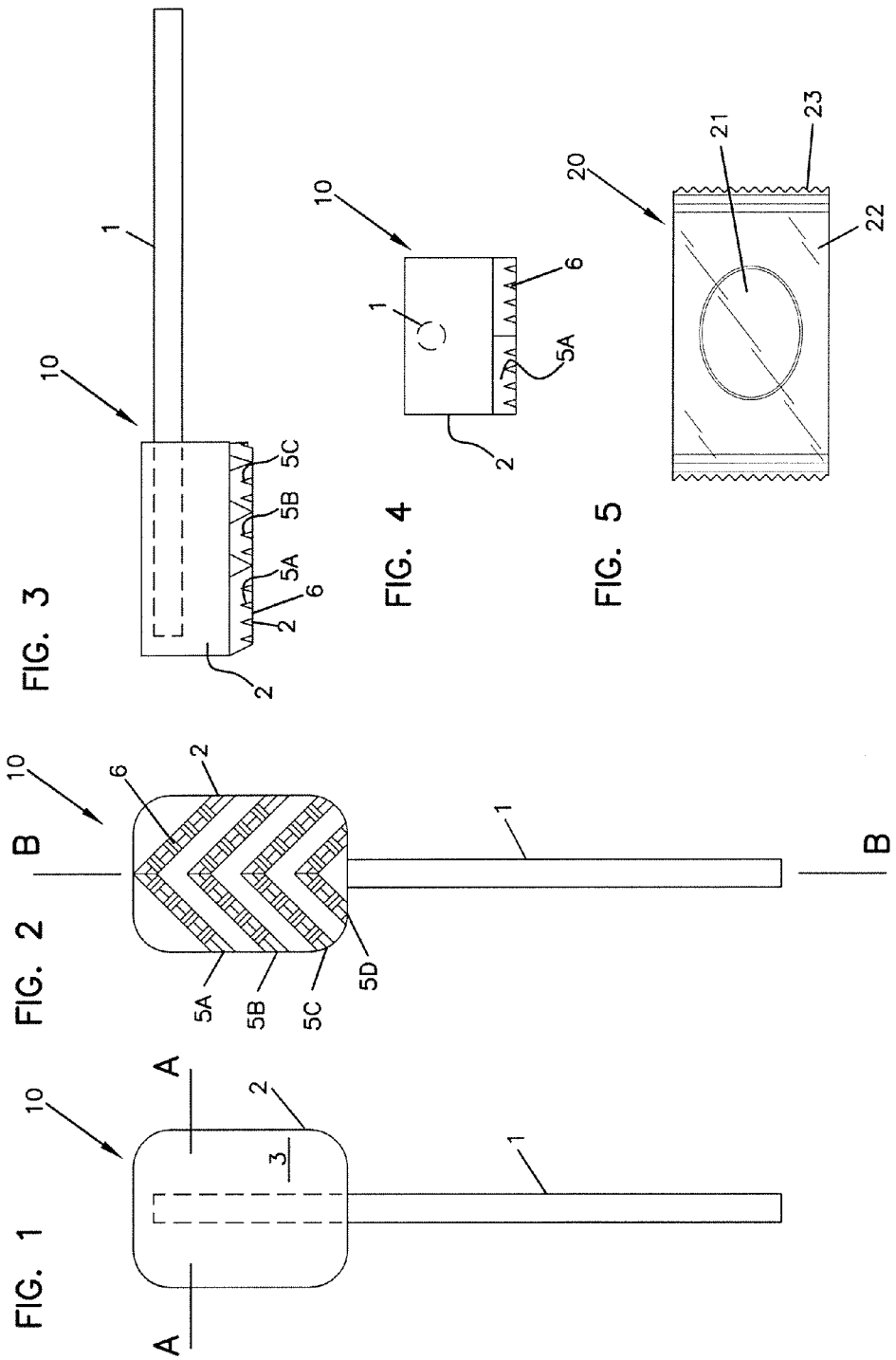

COMPOSITION WITH ACTIVATED CARBON IN ORAL TREATMENT

CROSS-REFERENCE TO RELATED APPLICATION

This application claims the benefit of U.S. Provisional Patent Application Ser. No. 60/812,175, filed Jun. 8, 2006, which application is hereby incorporated by reference it its entirety.

FIELD OF THE INVENTION

The invention relates to the technology of personal care compositions and specifically relates to compositions that can be introduced into or applied to the oral cavity of humans for treatment purposes. One purpose includes reducing or eliminating oral malodor regardless of etiology. Such odors can arise from healthy individuals but can also result from smoking, diet, disease, injury, drug or other pharmaceutical treatment, or other natural or artificial source. The treatment means of the invention is useful in any human social environment or work endeavor but is also useful to reduce malodor in a hunting context to improve hunting yields or outcomes. The treatment can obtain other advantages.

BACKGROUND OF THE INVENTION

The manifestation of malodor in the oral cavity of humans has been a problem facing humans in many types of interpersonal interactions for many years. Many attempts to either mask or remove such odors have been proposed in the art for many years. In large part, the technology has evolved in such a way that individuals attempt to use a mouthwash or other oral preparation for the purpose of reducing microbial populations that, in turn, further reduce the production of malodors. After malodors have been produced through a variety of mechanisms, people have attempted to use mouthwashes and other oral preparations to remove the odors and odor causing elements from the oral cavity reducing the occurrence of malodor. Further, compositions have been produced that effectively mask malodors simply by covering the odors with other materials that provide pleasant experience that overwhelms the negative impact of the malodors.

Such malodors are a problem in a variety of human endeavors including social contacts, professional and workspace contacts and the interaction between humans and the environment. In one particular context, malodors can cause failure and frustration during hunting in which the subject prey can detect the presence of hunters in the vicinity by detecting malodors. Many prey animals are very sensitive to certain odor or malodor and can often detect human breath malodors at low concentration and at great distance from the hunter's location. The natural oral microbial populations, flora or bacteria respire and transpire in the porous surface in the mouth and particularly on the tongue. These microorganisms can consume biologically available compounds present in saliva. As a result of the metabolism, the bacteria release malodor causing compounds. The presence of the bacteria and the associated compounds create the "hunter's breath" that many prey can detect. A number of specific attempts at preventing, reducing or masking malodors have been proposed in the art. Hunter's breath, which is the target malodor of the invention, arises typically from bacterial populations in the oral cavity. In large part the predominant location of the majority of microorganisms is on the rough and porous surface of the human tongue.

In one mode of malodor reduction, masking agents have been used but appear to only add to the odor causing materials in the oral cavity. Another mode uses absorbents or adsorbents to reduce or eliminate malodors. A variety of absorbents or adsorbents have been used including such materials as silica gel, zeolite absorbents and activated carbon.

Activated carbon has been known for many years and has been used for a variety of absorbent and adsorbent applications including reductions in the offensive odors produced in a variety of materials.

Activated carbon is discussed in the *Kirk-Othmer Encyclopedia of Chemical Technology*, Fourth Edition, Wiley & Sons, Inc. (1999) on pages 323-324. Activated carbon has been included in a variety of products.

Sauer, U.S. Pat. No. 1,542,006, which is a bad breath treatment for patients in which activated carbon is compounded into a pill or tablet with sugar as a binding agent. The tablet contains large amounts (90-94%) of carbon (see page 1, lines 49-55). The patent at page 3, lines 103-106 for the blending information.

Geils, U.S. Pat. No. 4,122,169, teaches a tablet containing activated carbon and sorbitol in a tablet form. This form has 5-20% carbon in a sorbitol base.

Nishimura, U.S. Pat. No. 4,761,284, teaches activated carbon in a compressed tablet that is used to absorb toxin materials from a poisoning victim in an antidote mode. Virtually the entire tablet is carbon. Similarly, the Scent Eraser® capsule is a gelatin capsule containing a major proportion of carbon and minor secondary ingredients such as chlorophyll and parsley.

Harwood, U.S. Pat. No. 6,861,049, teaches aqueous slurries of activated carbon (20 to 50%) useful for cleaning lingual surfaces.

Johnson, U.S. Pat. No. 6,440,415, teaches a spray, detergent, deodorant/mouthwash for hunter's odor or breath. The mouthwash contains a variety of typical mouthwash formulations including water, dye, flavorings and activated carbon (see Column 3, line 5 for the primary disclosure).

Sesselmann, U.S. Pat. No. 5,539,930, teaches the use of activated carbon in hunters' clothing to absorb human odors.

Lucas et al., U.S. Pat. No. 5,874,067, and Peterson et al., U.S. Pat. No. 5,861,144, teach materials used for controlling malodors on human skin.

A substantial need remains in personal care composition, treatment or odor reduction method providing a safe, effective, easily used, palatable treatment composition for human malodors arising from the oral cavity.

BRIEF DESCRIPTION OF THE INVENTION

The personal care treatment comprises a comestible, confection, lozenge, chewing gum or appliance. The typically soft chewable or hard comestible, candy or confection contains sufficient activated carbon for malodor reduction or elimination. Typically an effective amount is less than 25%, less than 10%, less than 8 wt %, or less than 5 wt % of activated carbon. This amount can absorb oral malodors and reduce or eliminate the release of malodors from the treated individual. The activated carbon capable of reducing or eliminating malodors is typically dispersed or suspended throughout the hard comestible, candy, confection or appliance. The composition and article can also contain other useful materials for treatment of the subject.

When used as a composition or lozenge, after insertion, as the confection is present in the oral cavity and is chewed or as it slowly dissolves in the oral cavity, the user experiences the pleasing sweet or optionally flavored release of the confection and any flavoring therein along with some proportion of the activated carbon dispersed or suspended throughout the confection. When used as an appliance, the composition is urged mechanically against the surfaces in the oral cavity releasing the confection and carbon. Once the activated carbon is released into the oral cavity, its substantial absorbent and adsorbent character can rapidly remove malodors and compounds that generate malodors that are present in the oral cavity treating the human subject and reducing the offensive character of the malodorous compounds. Other materials can also be included in the composition of the invention to act as a source of pleasing odor, as an attractant or to treat other problems in the oral cavity apart from malodor.

A first aspect is a malodor treating composition.

A second aspect is in a treatment article (e.g.) a gum or lozenge, comprising a soft or hard carbohydrate confection containing an effective amount of carbon.

A third aspect is an article the combines the carbon and other materials for treatment of the subject.

A fourth aspect is an abrasive appliance or abrasive cleaner for the oral cavity that can be brought into contact with surfaces within the oral cavity for the purpose of mechanically removing and eliminating both bacteria and the resulting bacterial metabolites comprising the malodor compounds. Such an appliance or cleaner can be made of the carbon containing materials of the invention.

For the purpose of this disclosure, the term "hard comestible," "hard candy" or "hard confection" are substantially synonymous and refer to a solid mass of a sugar, natural or artificial sugar substitute or a blend thereof that is made by blending a sugar source or sugar substitute at an elevated temperature with activated carbon and other active ingredients of the invention to form a rope which is then mechanically formed into individual pieces that harden and solidify into the objects of the invention. A "chewing gum" includes a confection in a typical natural or artificial polymer gum base and the malodor reducing composition. The mechanical appliance or cleaner is shaped and configured to abrade oral surfaces and remove both microbial populations and the associated odor. An "active ingredient" of the composition is any compound or material that is a medicament, a nutritious material, a malodor masking or pleasant or attracting odor imparting material, or generally any other ingredient that is not activated carbon, hardened carbohydrate, or a filler or flavoring.

BRIEF DESCRIPTION OF THE DRAWINGS

FIG. 1 is a plan view of one embodiment of the abrasive cleaner of the invention.

FIG. 2 is a second plan view of the abrasive cleaner of the invention.

FIG. 3 is a cross-section of the abrasive cleaner of the invention of FIG. 2, along the line B-B.

FIG. 4 is a cross-section of the abrasive cleaner of the invention of FIG. 2, along the line A-A.

FIG. 5 is a plan view of the packaged carbon containing article or lozenge.

DETAILED DISCUSSION OF THE INVENTION

The hard comestible or confection of the invention contains a substantial proportion of a confection base, an effective amount of activated carbon. Typically an effective amount is less than 25%, less than 10%, less than 8 wt % or less than 5 wt % of activated carbon. The composition can often contain an effective amount of one or more further treatment compounds. Such treatment compounds can include an odor mask, an odor absorbent, an antibacterial agent, flavors, perfumes, dyes, treatment materials that can aid in treating trauma, gingivitis, pain, congestion, cough, sore throat, allergy reaction, toothache, sores of the oral cavity (trench mouth) or any other surface that comes in contact with the confection of the invention. Accordingly, a preferred formulation for the composition of the invention comprises about 50 to 95 wt % of the confection base, about 0.01 to about less than 5 wt % of the activated carbon and from about 0.01 to about 45 wt % of the second treatment composition.

The size of the lozenge can be designed to provide substantial treatment for a period of time from about 5 minutes to about 1 hour or more depending on the confection base selected and the size of the lozenge. The lozenge of the invention contains as an active ingredient and activated carbon in an amount of about 0.01 to 4 wt % of the composition.

The chewing gum of the invention comprises a gum base and the carbon with optional active ingredients.

The active ingredient of the composition is any compound or material that is a medicament, a nutritious material, an odor masking or odor imparting material, or generally any other ingredient that is not activated carbon, hardened carbohydrate, or a filler or flavoring. For example, the active ingredient can be a medicine such as an antihistamine, a decongestant, and the like. The active ingredient can be a nutritious material such as a vitamin or mineral, an odor masking material such as chlorophyll or cyclodextrin, an odor imparting material, such as mint or an animal attractant, or any combination of these.

The activated carbon or activated charcoal is a solid, finely divided small particulate with substantial internal surface area in pore size or volume. The amorphous carbon provides extensive adsorptive properties that, once activated, can absorb a vast area of organic compound that can contribute to the production of human malodors in the oral cavity. Commercial activated charcoal or activated carbon is produced from carbon containing materials including coal, wood, pitch coat, lignite, etc. The materials are typically heated into a carbon form and then thermally or chemically activated. The important characteristics of the activated carbon include available surface area, pore size and size distribution, surface chemistry, particle size and particle density.

The activated carbon particle is typically spherical with substantial absorbent surface area and pore cavity. The typical particle size for activated carbon useful in this invention typically ranges from about 3 to about 500, preferably from about 5 to about 250 microns. The internal surface area which is important for the absorbent characteristics typically ranges from about 100 to about 1000 $m^2$-gm. Activated carbon or activated charcoal products can be obtained from a variety of sources. Norit Americas Inc. produces products denominated as Norit® A Supra, Norit® B Supra, and Norit® E Supra. These commercial products comprise carbon particles typically less than 150 microns in diameter. The amount and particle size of the carbon results in a palatable confection that has absorbent activity without causing a negative mouth feel.

The candy or confection base can be produced from materials such as sucrose, sucrose solids, corn syrup solids, fructose corn syrup, maltose, isomaltose, lactose, sucrose, polyfructose, dextrose, polydextrose, maltodextrin, sucralose, aspartame, acesulfame-K, saccharine, sorbitol, manitol or other sugary, natural or artificial confection-like preparation. Typically, the treatment units of the invention comprise at least 85-99 wt % of the confection base, more typically 90-95 wt % of the confection base. In order to vary the hardness or other properties of the lozenge, a variety of other materials can be used including starches, cellulose derivatives, gelatin, glycerin and others. Further, added materials such as magnesium or calcium stearate, edible clay such as montrnorillonite clay, or polyethylene glycols can be used to help promote the formulation of a tablet or lozenge.

The confection of the invention can contain the comestible or confection base and the effective amount of activated carbon for malodor control, but can also contain any other ingredient or additive useful in a preparation for oral treatment. Such materials include humectants, sweeteners, antibacterial agents, soothing agents, healing agents, flavors, perfumes, dyes, etc. Flavoring agents can include oils or extracts derived from natural, agricultural, plant or food sources including lemon oil, lime oil or orange extracts. Further, natural or synthetic flavoring materials include oils derived from lemon, honey, cherry, menthol, eucalyptus, peppermint, spearmint, licorice, ginger, fruit, cinnamon or a variety of natural oils or natural extracts.

The chewing gum of the invention can contain the comestible or confection conventional natural or synthetic polymer gum base and the effective amount of activated carbon for malodor control, but can also contain any other ingredient or additive useful in a preparation for oral treatment. Such materials include humectants, sweeteners, antibacterial agents, soothing agents, healing agents, flavors, perfumes, dyes, etc. Flavoring agents can include oils or extracts derived from natural, agricultural, plant or food sources including lemon oil, lime oil or orange extracts. Further, natural or synthetic flavoring materials include oils derived from lemon, honey, cherry, menthol, eucalyptus, peppermint, speannint, licorice, ginger, fruit, cinnamon or a variety of natural oils or natural extracts.

The confection of the invention can be used as is, but can also be used with an external coating. The external coating can be for appearance, protection, flavor, or a combination of these functions. Appearance functional coatings can be colored, for example, in a solid or multicolored format. A useful multicolored format is camouflage type coloration. Camouflage would be useful for hunters in the field, for example, to hide the lozenge from view. Another appearance functional coating can be a printed or stamped layer, wherein a logo, a picture, a word, or a combination of these communicates the source, manufacturer, or use of the lozenge. This is particularly useful in case two or more differing formulations are produced for differing use environments. Coloring agents used in the coatings or printed or stamped layers of the lozenge can include acceptable dye such as Blue Dye No. 1 or Dye No. 2, Red Dye No. 3, Red Dye No. 40, Yellow Dye No. 5, titanium dioxide or mixtures thereof. A protective coating could be a hard shell to protect the lozenge, or a powder coating to protect the lozenges from sticking together in high humidity environments. A flavor functional coating can be a layer that adds to the appeal of the lozenge. Such coatings can comprise a transparent GRAS coating, a chocolate coating, a flavored coating or other conventional exterior coating composition. Such a coating can comprise a legend or a design such as a camouflage print.

The composition and article can also include a variety of medical agents that can be used for additional activity against malodors and can further reduce microbial populations in the mouth. Other medicinal agents can also be alternatively used in lozenges of the invention. Typical such agents include pain relief agents, odor reducing compounds such as cyclodextrin, chlorophyll, antimicrobial compounds such as chlorohexadene, decongestants, antihistamines or expectorants for added relief. Other useful ingredients in the composition of the invention include antitussive compositions, medicaments used in conventional cough and cold remedies including topical anesthetics, throat soothing agents such as ethylaminobenzoate diperodon hydrochloride, benzocaine, etc. Benzyl alcohol is often used in pharmaceutical compositions as a topical anesthetic or soothing agent. In such applications, benzyl alcohol can be combined with dextromethorphan for a useful throat soothing anti-cough preparation. The confection of the invention can also contain skin protectants, emollients and other such materials that can soothe the oral cavity. Such materials include saturated or hydrogenated oils that can often be combined with hydrophobic antibacterials. Skin protecting or softening agents can include Vitamin A, cod liver oil, cocoa butter, shark liver oil, petrolatum, white petrolatum, mineral oil, jojoba oil, lanolin and other materials. The manufacture of the article of the invention can also be improved using GRAS or food grade emulsifiers. Such emulsifiers can be in the form of a surfactant, typically in the form of a non-ionic, anionic or cationic surfactant. The lozenge of the invention can include conventional non-steroidal anti-inflammatories including ibuprofen, naproxen sodium, ASA, acetaminophen, Tylenol and other similar compounds. The lozenge of the invention can include other conventional additive ingredients including such compounds as caffeine, alkaline metal and alkaline earth metal fluoride, sources of zinc, cetylpyridium chloride, vitamins including vitamins B12 and C and natural ingredients such as ginseng, *ginkgo biloba, Echinacea* and others.

The composition and article can also contain a variety of medical agents that can aid in reducing the symptoms of coughs, flu and allergy. Other symptoms include itchy eyes, runny nose, congestion, etc. Such a treatment is particularly useful for hunters. The composition or article in the invention contains carbon that can reduce malodor while the additional medical agents can be used to reduce cough, post nasal drip, sneezing, itchy eyes and other symptoms that can manifest itself. Such medical agents include cough suppressants, expectorants, decongestant, antihistamine compositions and the NSAID materials discussed elsewhere. Cough suppressants that can be used in the compositions and articles of the invention include dextromethorphan, noscapine, or isoaminile codeine, hydroquinone, caramenephyne, carbetapentane or others available for cough suppression. Alternatively, an expectorant such as guaifenesin or other soothing materials such as menthol or eucalyptus oil can be incorporated to relieve congestion. Antihistamines that can be used in the compounds of the invention include diphenhydramine hydrochloride or dexchlorpheniramine maleate, chlorpheniramine maleate and clemastine. Decongestions useful for use in the invention include ephedrine, Phenylephrine, phenylpropanolamnie, pseudoephedrine, oxymetazoline, naphazoline, xylometazoline, propylhexyldrine or levo-desoxy-ephedrine.

These decongestants can reduce nasal congestion and runny nose arising from colds, flu and allergies. Decongestants can constrict blood vessels and reduce blood volume and the associated fluid that can leak under the influence of histamines. Antihistamines can slow the release of histamine from natural tissues and reduce the allergic reaction. Decongestants typically tend to counter affect the effects of antihistamines.

Antimicrobials can be used to reduce the oral population of microbes, but can also be used as preservatives for the composition of the invention. Such ingredients include biocidal or biostatic compounds. These materials are typically used in an amount of less than 1%, typically from about 0.01 to 0.3%. Preferred antimicrobials are antibiotics and anti fungal that have at least some substantial water solubility and can be dissolved in saliva of the oral cavity. Such materials are well known in the art and are described in, for example, "The Theory and Practice of Industrial Pharmacy", Lockman et al., Third Edition and Pilosf et al., U.S. Pat. No. 5,534,165. Materials that are effective in treating both the gram deposit and gram negative microorganisms and fungi are often very useful. The confection of the invention can also be preserved using preservative materials. Such materials include Nystatin, sodium benzoate, benzyl alcohol, quaternary ammonium compounds, chlorohexadene or other GRAS or food grade materials.

The hard confection of the invention can also comprise other ingredients for specialized purposes. For example, if the user of the confection is a hunter who is hunting deer, then the confection could also contain substances to help attract deer. Clover, corn, soybean, chicory, and *brassica* are plants that are desirable food to deer. A chicory essence added to the confection of the invention, for example, can help attract deer to the hunter's location, as the hunter's breath would smell like clover to the deer.

A suitable treatment lozenge for oral administration can be made by typically combining carbon and other active ingredients or additives with a solidifiable carbohydrate or confection base. A useful premix can be made of the actives that can then be combined with the confection base. The appliance of the invention can also be made by using the composition of the invention alone or with conventional handles, wrappers and packaging.

The composition can be coated with sugar solutions that can contain thickeners, pigments, dyes or other useful additives. Dyestuffs can be added to the coatings if a colored (non-black) lozenge is desired. Typically, the candy or confection mass is often blended from dry ingredients and then warmed until it is soft and can be manufactured using common lozenge forming machinery. Typically, an amount of the warmed confection mass containing the carbohydrate base and the carbon combined with other active ingredients are combined and kneaded or mixed in a very high viscosity syrup until formable. The formable mixture is typically transferred to a machine that typically forms the warm confection into a formable rope. The rope can then be converted into lozenges using typically lozenge forming equipment. The lozenges, once formed are then cooled and packaged. Alternatively, the lozenge after formation can be coated with a coating that can provide a transparent or colored exterior to the lozenge. The lozenges can be formed in sizes that range from about 0.2 gram to as much as 50 grams.

The compositions of the invention can be used for the treatment of a variety of human problems including, gingivitis, acute necrotizing ulcerative gingivitis, oral pain, periodontal disease, soft tissue trauma, canker sores, etc. by applying a lozenge of the invention to the oral cavity of an individual needed therapy and permitting contact between the active substances in the composition and the site(s) of the problem.

The invention also contemplates an abrasive cleaner for an oral cavity. The abrasive cleaner is shape and configured such that it can contact surfaces in the oral cavity for the purpose of obtaining sufficient abrasive action and mechanical force to dislodge, remove, absorb, adsorb, or otherwise mechanically disturb both the bacterial populations and malodor compounds from the surface for the purpose of removing them.

Once bacterial populations and malodor compounds are mechanically removed or abraded from oral surfaces, the person can remove such bacteria and odors in any convenient fashion. The user can use the carbon containing oral confection of the invention as a malodor absorbent or preventer. Alternatively, the abrasive cleaner of the invention can be fabricated from the composition of the invention such that the composition can be used both as an abrasive and as an odor preventer or absorber.

Regardless of the composition of the abrasive cleaner, the cleaner structure requires at least an abrasive surface that can apply mechanical actions to the surfaces of the oral cavity for the purpose of dislodging bacterial populations and malodor compounds. The abrasive surface can comprise a variety of different abrasive structures. The abrasive structures can comprise a random or regular distribution of raised portions in a pattern. The pattern can either be random or can have an ordered array of raised areas. Each raised area can, in turn, have a structure. The raised areas can be semicircular, can be circular, can be pyramidal or can have any appropriate shape extending from the surface of the body into the shape of the abrasive element. The body of the abrasive cleaner can also have a set of larger portions that extend from the body to form a scraper. In such a configuration, the body can have one, two, three or more portions extending from the body in a scraper structure. In one embodiment, the scraper portions can comprise simply a portion in the form of a triangular shape extending from the body or in the triangle is a cross-section of the extended portion. One or more of these triangular portions can be formed on the body and the peak of the triangle can act as the abrasive surface. The structures can be formed in a linear manner or can have a V-shaped or zig-zag shape as the shape extends across the surface of the body. One preferred mode of forming the scraper portion of the article is the use of a portion in the form of a chevron or chevrons formed in the surface of the structure.

FIG. 1 shows one embodiment of a top view of the structure of the invention. The scraper of the invention includes the scraper 10 of the invention includes handle 1 and the abrasive body 2. The top view of abrasive cleaner 10 can be either smooth the top view 3 can be smooth or it can have an abrasive surface.

FIG. 2 is a view of the opposite side of the abrasive article and shows again handle 1 and a body 2 except that the view shows four chevron scraper portions 5A, 5B, 5C and 5D in the form of chevrons with serrations 6 displayed along the body 2.

FIG. 3 is a cross-section of the FIG. 2 taken along line B-B. In FIG. 3 is shown the handle 1, body 2 and the scraper or abrasive portions 5A, 5B and 5C with serrations 6.

FIG. 4 has a cross section of FIG. 1 taking along line A-1. In FIG. 4 is shown handle 1, body 2, and a view of the scraper or abrasive portion 5A and serrations 6. Also shown in FIG. 4 are the serrated edges formed in the serrated edges for formed in the chevron portions 5A. The abrasive surface for example of FIG. 2 having an array of abrasive portions 5A, 5B, 5C and 5D each abrasive portion having serrated edges 6 forms a highly effective abrasive surface. Such abrasive surface can be used to treat virtually any surface of the oral cavity for the purpose of removing bacteria and other compositions, providing surface area for the release of the odor absorbing carbon or the other active medical agents of the composition or article of the invention. The article shown in FIGS. 1-4 can be used in a method of treating the oral cavity or in the article 10 contacted with a surface of the oral cavity and is used in an abrasive mode mechanically contacting surfaces of the oral cavity for the purpose of removing bacteria and releasing malodor absorbent carbon and other medical agents.

Handle 1 shown in FIGS. 1-4 can be made of virtually any substance that is useful in both acting as a handle for the abrasive cleaner of the invention but can also be used in a shaping or molding step in which the scraper portion 2 is formed and combined with the handle in a manufacturing process. Accordingly, such a handle can be made from paperboard, wood, plastic members, or can be made from the absorbent composition of the invention. The handle 1 can contain markings and colorants such as a solid color that is the same or different from the external or internal color of the body 2, a pattern such as a pattern similar to the pattern on the body 2, a marking with a logo or picture, or a combination of markings and colorants.

FIG. 5 shows an article 20 of the invention comprising a hard confection or lozenge 21 in a clear package 22. The package is closed conventionally with a sealed end 23.

The abrasive appliance or cleaner body structure containing the abrasive portions is preferably made from a structure containing an absorbent or odor treating material such that the scraper can both act as an abrasive cleaner and as an absorbent for the malodor compositions.

The abrasive appliance or cleaner structure of the invention can be made with well-known confectioner candy making techniques in which the initial formulation of the composition is typically made in semi-liquid or syrup form and hardened conventionally in candy making equipment. Such equipment is also well designed and constructed such that the handles can either be molded simultaneously with the cleaner body or a separate handle can be included in the manufacture and combined with the cleaner structure. Such equipment is discussed additionally in other parts of the specification.

EXPERIMENTAL

Example 1

One preferred form of the invention can be made by a two step process involving a premix of the activated material combined with a confection base and passed through a machine that can form the total composition into a useful form such as a lozenge. In the manufacture of the premix, about 39.6 parts by weight of a 96% active USP glycerin (balance water) is combined with 59.4 parts by weight of activated carbon combined with 0.99 parts by weight of chlorophyll. In making the premix, glycerin is introduced into a Hobart stainless steel mixing bowl with stirrer. Activated carbon is added to glycerin with agitation. The carbon is added in small portions with the glycerin absorbing the carbon slowly during mixing between additions. After the activated carbon has been successfully added, chlorophyll is added slowly in step 3 and the resulting mixture is agitated until uniform. The manufacture of the premix requires substantial agitation of the mixture to ensure that the activated carbon is well mixed and dispersed throughout the glycerin mass.

In order to produce the treatment objective of the invention, the premix is combined with a mixture of sucrose and corn syrup in liquid form. First, about 60 parts by weight of liquid sucrose is combined with about 40 parts by weight of corn syrup comprising a glucose. The sucrose and corn syrup are mixed until substantially uniform. Once the combined candy base is mixed in uniform, the candy base is combined with the activated carbon premix in a ratio of about 5.3 parts of the premix per each 100 parts of the confection base comprising 60% sucrose and 40% glucose. The mixture is agitated and kneaded until the mass attains uniform color and consistency. The material is then rolled into a rope sized into an appropriate dimension, the rope is formed into a lozenge size of about 80-100 grams per lozenge. Once formed, the warm lozenges are cooled, packages and ready for shipment.

The product of the manufacture of a lozenge of the invention has a rough surface characterized by the presence of surface carbon and ridges, pits, crevasse and other surface imperfections. The surface features obtain a cleaning action when in contact with a surface or surfaces of the oral cavity. The scrubbing action can help clean the tongue or other surface to enhance the antimicrobial value or other action of the active ingredients.

Example 2

Example 1 is repeated except that after the mixture is agitated and kneaded until the mass obtains uniform color and consistency, the mass is divided into portions and each portion is combined with a paper or wooden stick using conventional confection forming techniques.

Example 3

Example 1 is repeated except that the premix comprises about 39.6 parts by wt. of a 96% active USP glycerin, 59.4 parts by wt. of activated carbon, 0.1 parts by wt. of dextromethorphan combined with 0.89 parts by wt. of chlorophyll.

Example 4

Example 1 is repeated except that the premix included about 39.6 parts by wt. of glycerin, 59.4 parts by wt. of carbon, 0.4 parts by wt. of a nonsteroidal anti-inflammatory and 0.59 parts by wt. of chlorophyll.

Example 5

Example 4 is repeated except that the NSAID was replaced by 0.4 parts by wt. of the combination of 0.2 parts by wt. of dextromethorphan, maleate and 0.2 part by wt. of pseudo ephedrine.

The above specification, examples and data provide a complete description of the manufacture and use of the composition of the invention. Since many embodiments of the invention can be made without departing from the spirit and scope of the invention, the invention resides in the claims hereinafter appended.

I claim:

1. A method of reducing malodor in breath from an oral cavity needing treatment, the method comprises administering a solid, abrasive and molded comestible composition having an abrasive surface to the oral cavity needing treatment, the molded comestible composition consisting essentially of:
    50 to 99 wt % hardened carbohydrate consisting essentially of sucrose and corn syrup, in which about 0.01 to about 4 wt % of a carbon malodor absorbent with a diameter of less than 150 microns and about 0.001 to about 45% of a chlorophyll compound with activity against malodors or anti-microbial activity is dispersed;
    and abrading the oral cavity.

2. A method of reducing malodor in the breath of a human hunter needing treatment, the method comprises administering a solid, abrasive and molded comestible composition having an abrasive surface to the oral cavity of a human needing treatment, the molded comestible composition consisting essentially of:
    50 to 99 wt % hardened carbohydrate consisting essentially of sucrose, corn syrup and glycerin in which about 0.01 to about 4 wt % of a carbon malodor absorbent with a diameter of less than 150 microns and about 0.001 to about 45% of a chlorophyll compound with activity against malodors or anti-microbial activity is dispersed; and abrading an oral surface.

3. The method of claim 1, wherein the composition comprises about 0.01 to about 4 wt % of glycerin.

4. The method of claim 1, wherein the composition further comprises a compound selected from an antimicrobial, an antihistamine, a cough suppressant, a decongestant or mixtures thereof.

5. The method of claim 4, wherein the antimicrobial comprises chlorhexidene.

6. The method of claim 2, wherein the composition comprises about 0.01 to about 4 wt % of glycerin.

7. The method of claim 2, wherein the composition further comprises a compound selected from an antimicrobial, an antihistamine, a cough suppressant, a decongestant or mixtures thereof.

8. The method of claim 7, wherein the antimicrobial comprises chlorhexidene.

9. A method of reducing malodor in the breath of a human hunter needing treatment, the method comprises;

administering a solid, abrasive and molded comestible composition having an abrasive surface to the oral cavity of a human needing treatment, the molded comestible composition comprising of:

50 to 99 wt % hardened carbohydrate comprising essentially of sucrose, corn syrup and glycerin in which about 0.01 to about 4 wt % of a carbon malodor absorbent with a diameter of less than 150 microns about 0.001 to about 45% of a chlorophyll compound and about 0.001 to about 45% of an active ingredient selected from a pain relief agent, an antimicrobial, a cough suppressant, decongestant, antihistamine, an expectorant, NSAID, or mixtures thereof;

and abrading an oral surface.

* * * * *